US008449184B2

(12) United States Patent
Diaferia et al.

(10) Patent No.: US 8,449,184 B2
(45) Date of Patent: May 28, 2013

(54) ROBOTIZED SYSTEM FOR POSITIONING A PATIENT WITH RESPECT TO AT LEAST ONE PARTICLE SOURCE

(75) Inventors: Leonardo Diaferia, Ruvo di Puglia (IT); Vincenzo Dimiccoli, Barletta (IT)

(73) Assignee: Itel Telecomunicazioni S.R.L., Ruvo di Puglia (BARI) (IT)

( * ) Notice: Subject to any disclaimer, the term of this patent is extended or adjusted under 35 U.S.C. 154(b) by 343 days.

(21) Appl. No.: 12/836,100

(22) Filed: Jul. 14, 2010

(65) Prior Publication Data

US 2011/0029129 A1 Feb. 3, 2011

(30) Foreign Application Priority Data

Jul. 28, 2009 (IT) .............................. MI2009A1344

(51) Int. Cl.
| | |
|---|---|
| *G06F 19/00* | (2011.01) |
| *A61G 13/02* | (2006.01) |
| *A61N 5/10* | (2006.01) |
| *B25J 9/00* | (2006.01) |

(52) U.S. Cl.
CPC ............ *A61N 5/1078* (2013.01); *A61N 5/1049* (2013.01); *B25J 9/0018* (2013.01); *B25J 9/009* (2013.01); *A61N 2005/1087* (2013.01); *A61N 2005/1089* (2013.01)
USPC ................... 378/209; 700/245; 5/601; 5/607; 5/608; 5/621; 378/208

(58) Field of Classification Search
CPC ........ B25J 9/0084; B25J 9/0087; B25J 9/0018; B25J 9/009; A61N 5/1049; A61N 5/1078; A61N 2005/1087; A61N 2005/1089
USPC ...................... 5/601, 608, 621; 378/208, 209
See application file for complete search history.

(56) References Cited

U.S. PATENT DOCUMENTS

| | | | | |
|---|---|---|---|---|
| 6,094,760 | A | * | 8/2000 | Nonaka et al. ...................... 5/601 |
| 6,193,142 | B1 | * | 2/2001 | Segawa et al. ................ 219/148 |
| 2003/0021386 | A1 | | 1/2003 | Tanaka |
| 2004/0133983 | A1 | | 7/2004 | Newkirk et al. |
| 2005/0234327 | A1 | * | 10/2005 | Saracen et al. ................. 600/407 |

(Continued)

FOREIGN PATENT DOCUMENTS

| | | |
|---|---|---|
| DE | 20315402 U1 | 4/2004 |
| DE | 20 2004 017881 | 3/2006 |
| WO | WO 00 71292 | 11/2000 |

OTHER PUBLICATIONS

Italian Search Report, MI20091344, filed Jan. 12, 2010.

(Continued)

*Primary Examiner* — James Trammell
*Assistant Examiner* — Todd Melton
(74) *Attorney, Agent, or Firm* — Young & Thompson

(57) ABSTRACT

A robotized system (1) for positioning a patient with respect to at least one source of a particle beam, includes the at least one source, two robotized arms (3, 4), a treatment couch (5) for the patient and a logic unit which controls and coordinates the movements of the two robotized arms, wherein
the at least one source is fixed,
each end of the treatment couch (5) for the patient is connected to the end of one of the robotized arms (3, 4),
the at least one particle beam emitted by the at least one fixed source is always included within the space between the ends of the two robotized arms (3, 4).

20 Claims, 9 Drawing Sheets

U.S. PATENT DOCUMENTS

Figure 1:
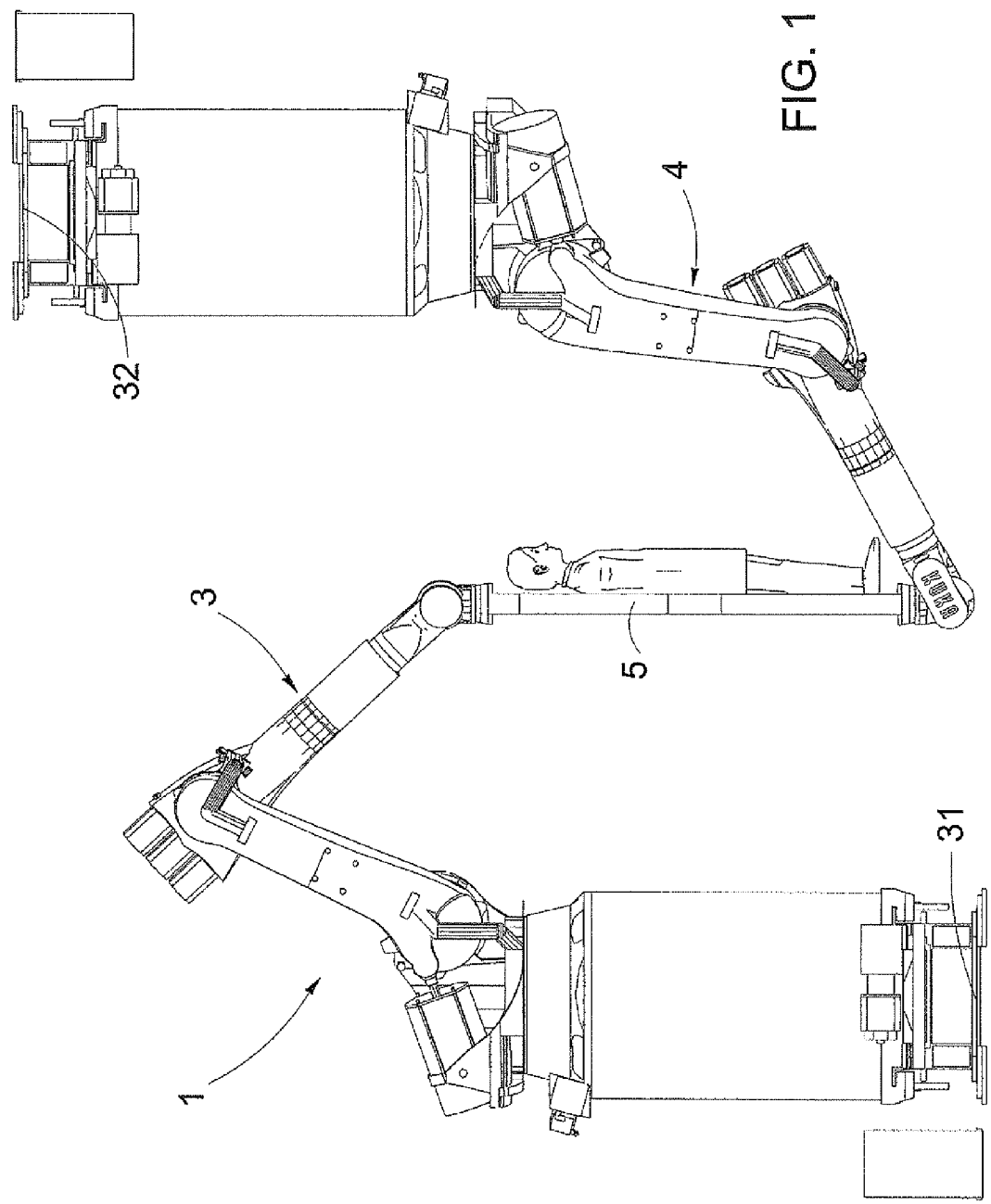

| | | |
|---|---|---|
| 2006/0185090 A1 | 8/2006 | Jackson |
| 2007/0003021 A1* | 1/2007 | Guertin et al. ............... 378/208 |
| 2007/0192960 A1 | 8/2007 | Jackson |
| 2007/0230660 A1* | 10/2007 | Herrmann ...................... 378/65 |
| 2008/0042076 A1* | 2/2008 | Miller et al. ............... 250/491.1 |
| 2008/0234865 A1* | 9/2008 | Sommer ....................... 700/258 |
| 2008/0292053 A1* | 11/2008 | Marash et al. ................... 378/65 |
| 2008/0317216 A1* | 12/2008 | Lifshitz et al. ............... 378/209 |
| 2009/0070936 A1* | 3/2009 | Henderson et al. ............... 5/601 |
| 2009/0123264 A1* | 5/2009 | Hartmann et al. ......... 414/798.2 |

OTHER PUBLICATIONS

European Search Report in Corresponding Application No. EP 10169458 Dated Sep. 2, 2010.

* cited by examiner

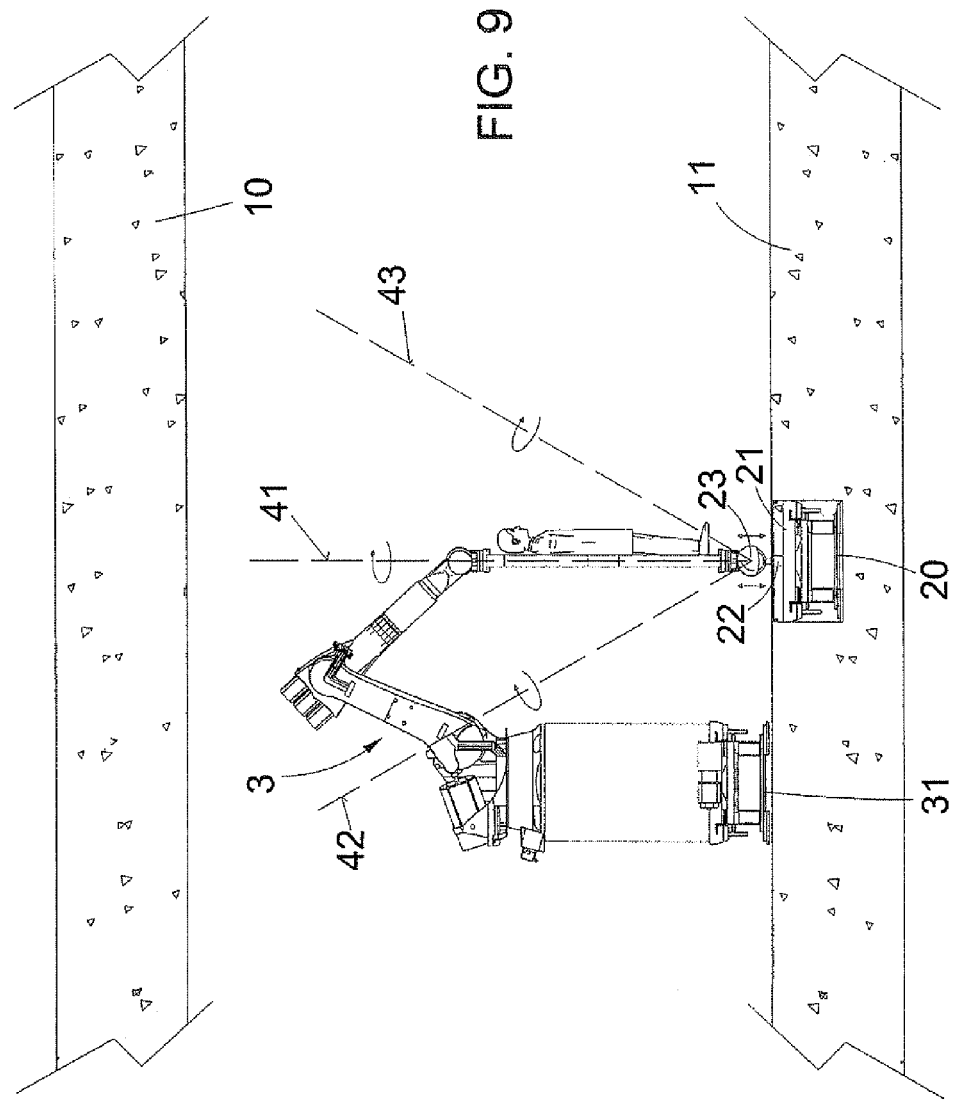

ROBOTIZED SYSTEM FOR POSITIONING A PATIENT WITH RESPECT TO AT LEAST ONE PARTICLE SOURCE

The present invention relates to a robotized system for positioning a patient with respect to at least one source of a particle beam (such as, for example, protons, light ions, photons, electrons, etc.) that have been proven to be effective for the treatment of diseases such as cancer, for example.

Apparatuses are known for treating such diseases by way of particle beams that include—besides the at least one source (not described herein since per se known) that emits a beam of particles as collimated as possible—means for adjusting the relative position of the at least one source of a particle beam and a treatment couch that carries the patient, so that the at least one particle beam hits the target exactly (i.e. the patient's tissues to be irradiated) without affecting (or affecting as little as possible) the surrounding healthy tissues.

The methods and apparatuses used to identify, within the patient's body, the position and size of the target and the procedures for determining the intensity and duration of the particle beam to be supplied in each session will not be discussed herein since such methods and apparatuses are per se known.

Once the location of the target is acquired, it is necessary to position the patient with respect to the at least one source so that the at least one beam can hit the target as foreseen by the treatment plan, without affecting tissues (such as, for example, gonads) that are (or can be) seriously damaged by the smallest possible particles and affecting as little as possible the healthy tissue surrounding the target.

To comply as much as possible to the treatment plan, the patient's body can be moved with respect to the at least one source so that the target is hit by the at least one particle beam for the entire duration of the session.

In many devices currently in use the at least one source of a particle beam is carried from a structure (called "gantry")—usually consisting of a hemispheric metal structure having a varying diameter from three to twelve meters and being strong enough to carry the at least one source of a particle beam—which allows the at least one source to move with respect to the patient's body as desired by the physician performing the treatment.

These devices are expensive, bulky and have "dead areas" (i.e. portions of the space around the patient's body unreachable by the at least one particle beam source) that do not always permit to optimally position the at least one source of a particle beam with respect to the body of the patient.

To overcome these serious drawbacks, devices have been proposed in which the patient, fastened to a treatment couch carried by a robotized arm, is moved with respect to the at least one source of a particle beam.

WO 2009/036169 describes a robotized arm having five axes of rotation and one axis of vertical translation carrying the treatment couch: if the jack which forms the axis of vertical translation is fixed to the floor without being supported by a column, the robotized arm does not have "dead areas". Such a robotized arm however does not allow to place the treatment couch near the floor and in any case at a height less than the length of said jack when fully retracted, nor to make a 360° axial rotation of the treatment couch or a vertical positioning of the patient or irradiate the back of the patient. Furthermore, a cylindrical volume obtained by axially rotating the treatment couch by 360° is not free from mechanical elements or other obstacles.

WO 2006/124434 describes a device comprising at least a one first robotized arm carrying the treatment couch, a second robotized arm carrying a source of a particle beam and a logic unit that controls and coordinates the movements of the two robotized arms to position, if possible, the patient with respect to the source of the particle beam. In fact, the treatment couch, the source of the particle beam and/or the robotized arms that carry them can interfere with each other, creating "dead areas" that hinder the optimal positioning of the patient with respect to the source of the particle beam (or vice versa). Such a device also has the same drawbacks of the robotized arm described by WO 2009/036169.

DE 20 2004 017 881 U1 describes a robotized system for taking a car off the production line and moving it to another work platform by executing a vertical and horizontal translation of the car.

US 2004/0133983 A1 describes a surgery table, in particular a surgery table that can be arranged for various types of orthopedic surgery.

The object of the present invention is to achieve a robotized system for positioning a patient with respect to at least one fixed source of a particle beam that is free from the limitations and drawbacks presented by known positioning systems.

In particular, one object of the invention is to provide a robotized system allowing the positioning of the patient in any position of the space without constraints in the volume between the arms of the system.

Another object of the invention is to provide such a robotized system that allows, in any position of the space as defined above, a full 360° rotation of the patient around its longitudinal axis.

The above mentioned objects are achieved through a robotized system that presents the characterizing features specified in the independent claim 1.

Further advantageous features of the invention form part of the dependent claims.

A robotized system according to the invention comprises at least one fixed source of a particle beam, two robotized arms, a treatment couch for the patient and a logic unit which controls and coordinates the movements of the two robotized arms.

Each end of the treatment couch is connected to one end of the robotized arms and the at least one particle beam emitted by the at least one fixed source is always included in the space between the ends of the two robotized arms.

Figure 2:
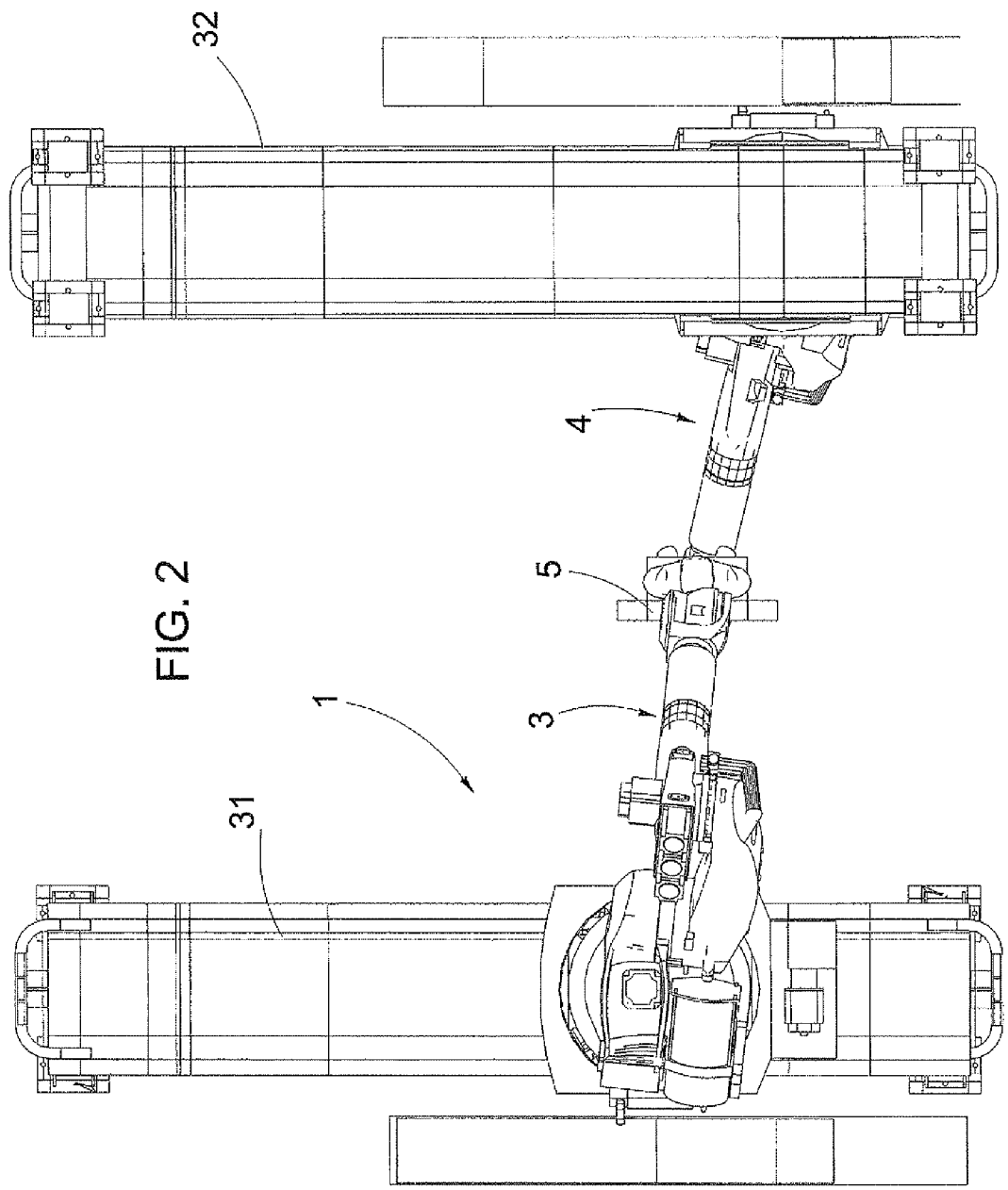
Figure 3:
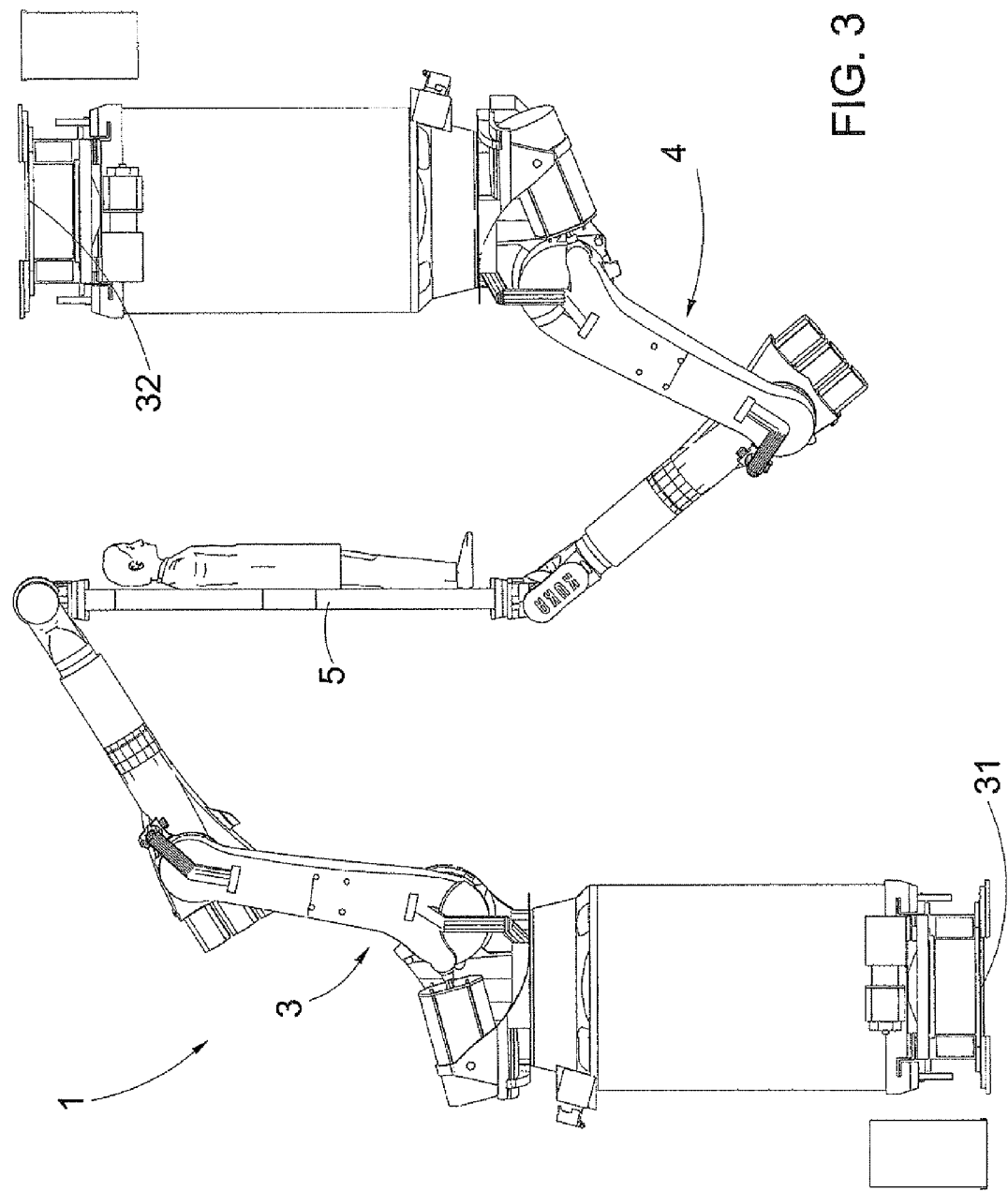
Figure 4:
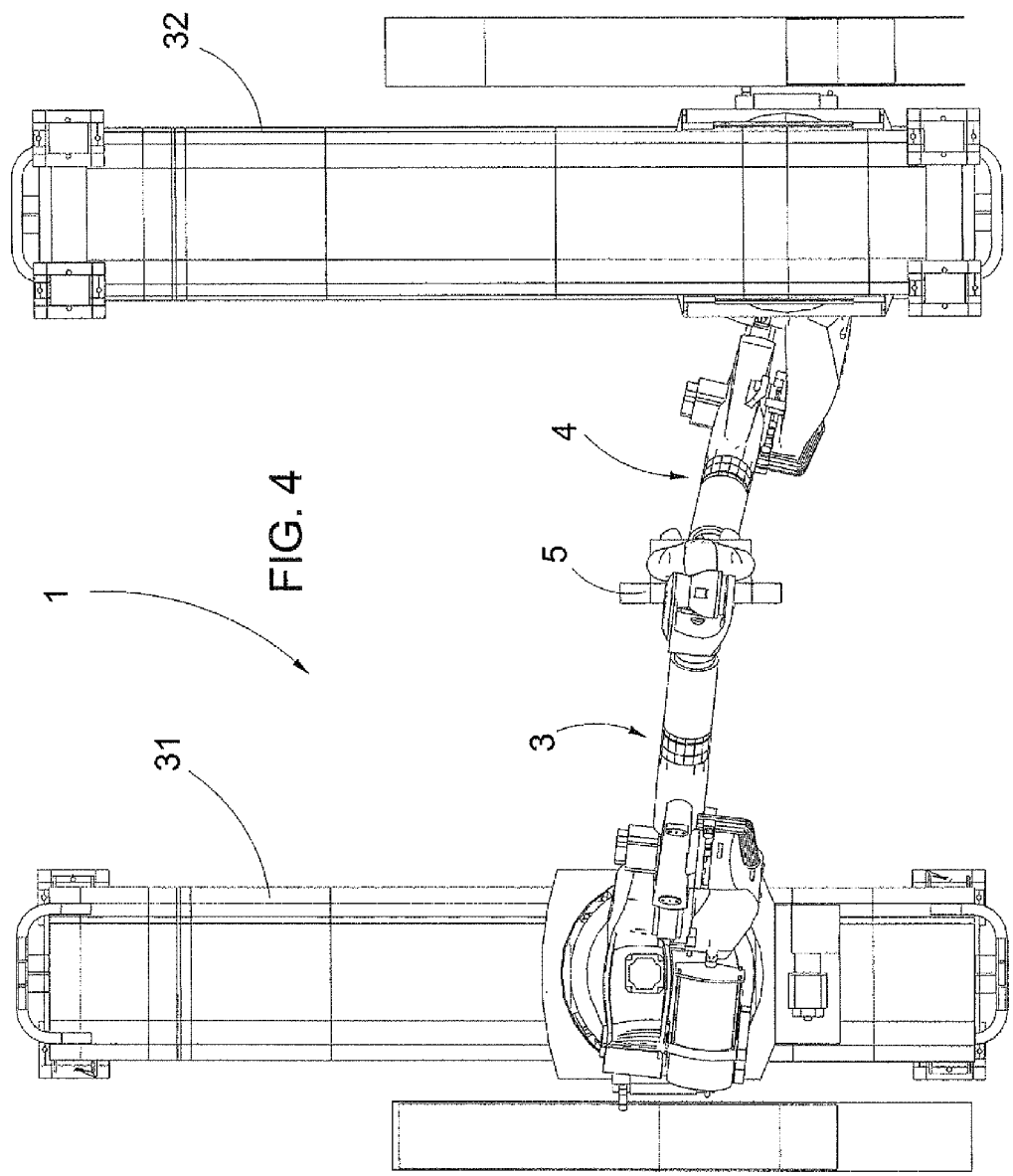
Figure 5:
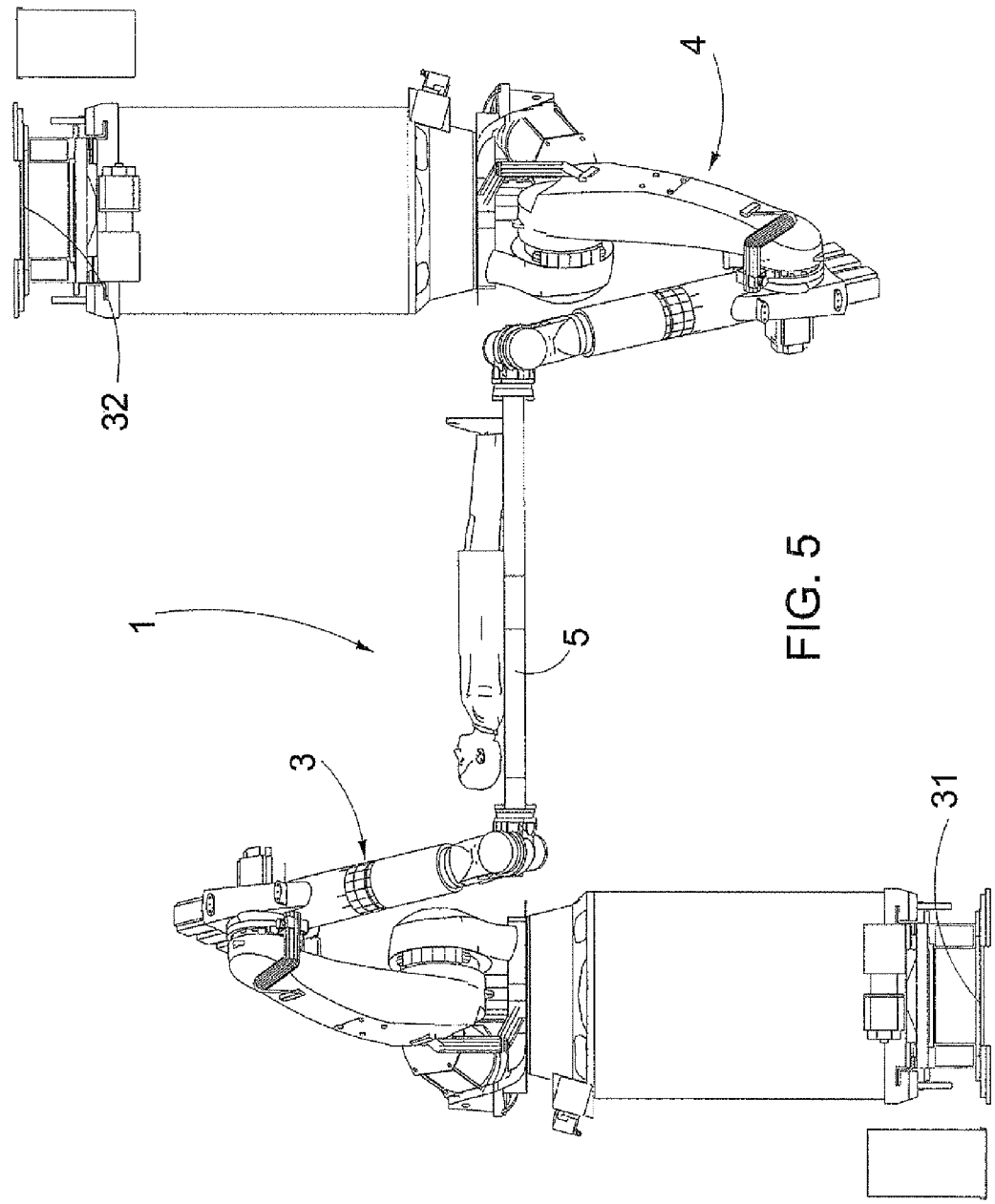
Figure 6:
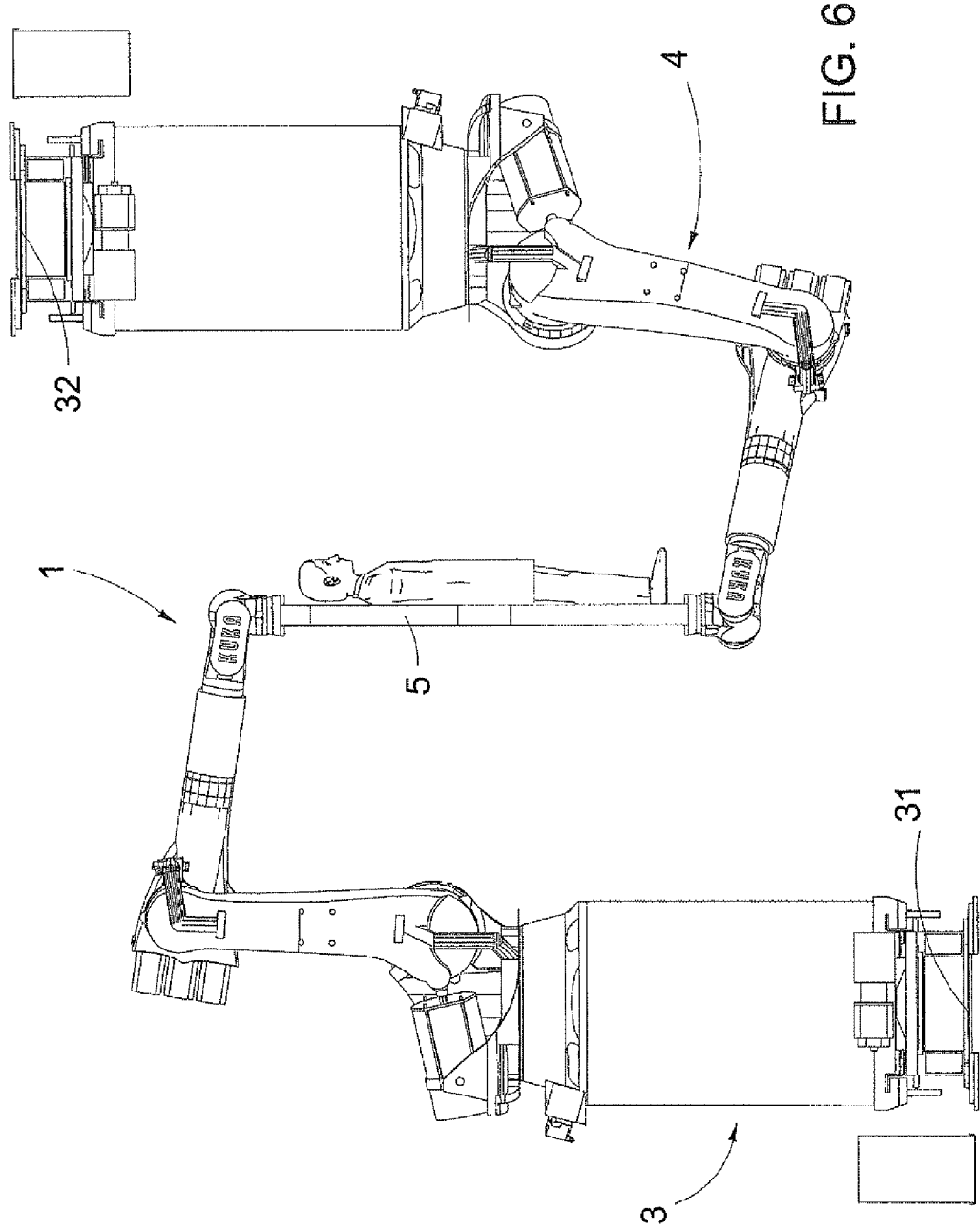
Figure 7:
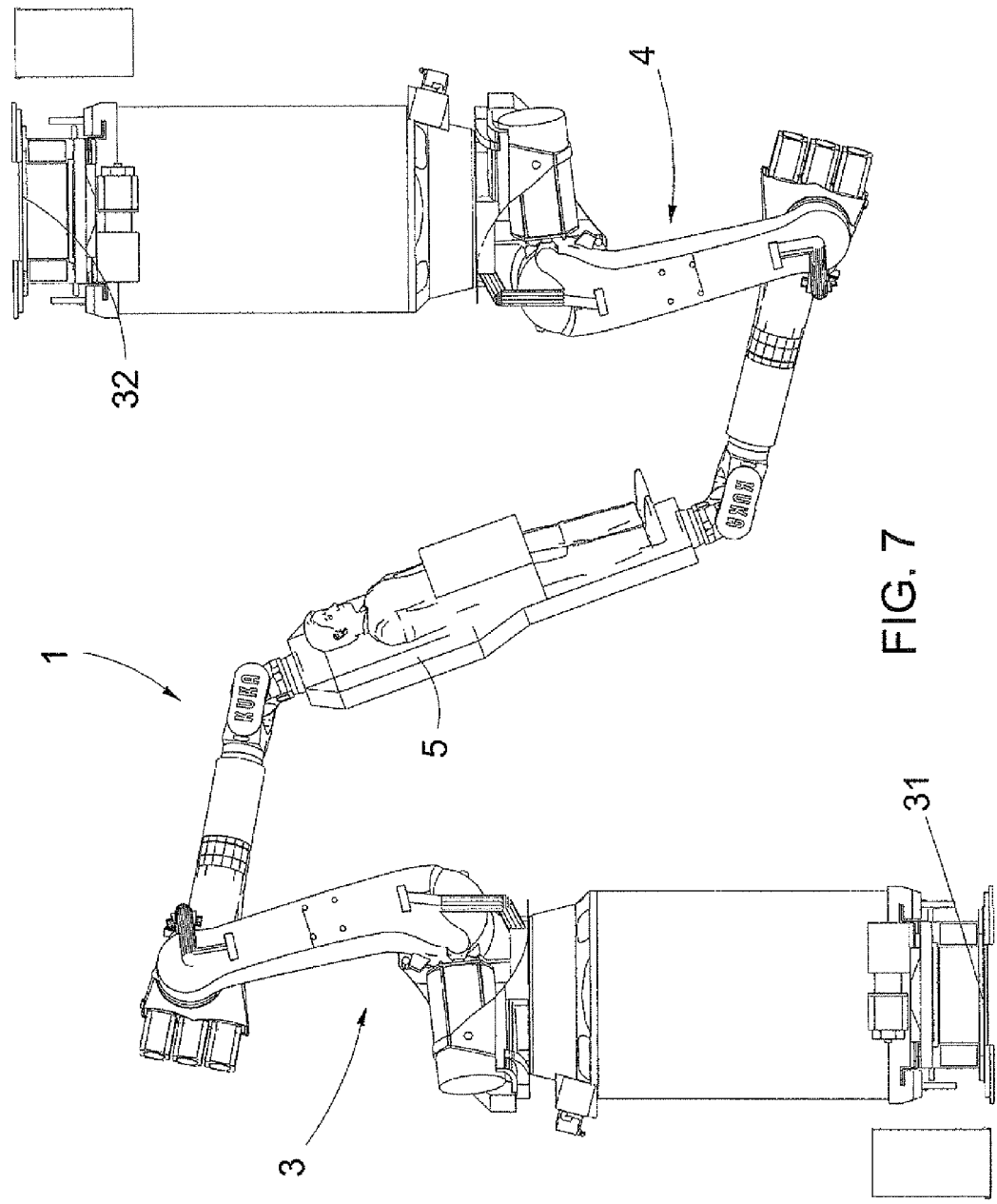
Figure 8:
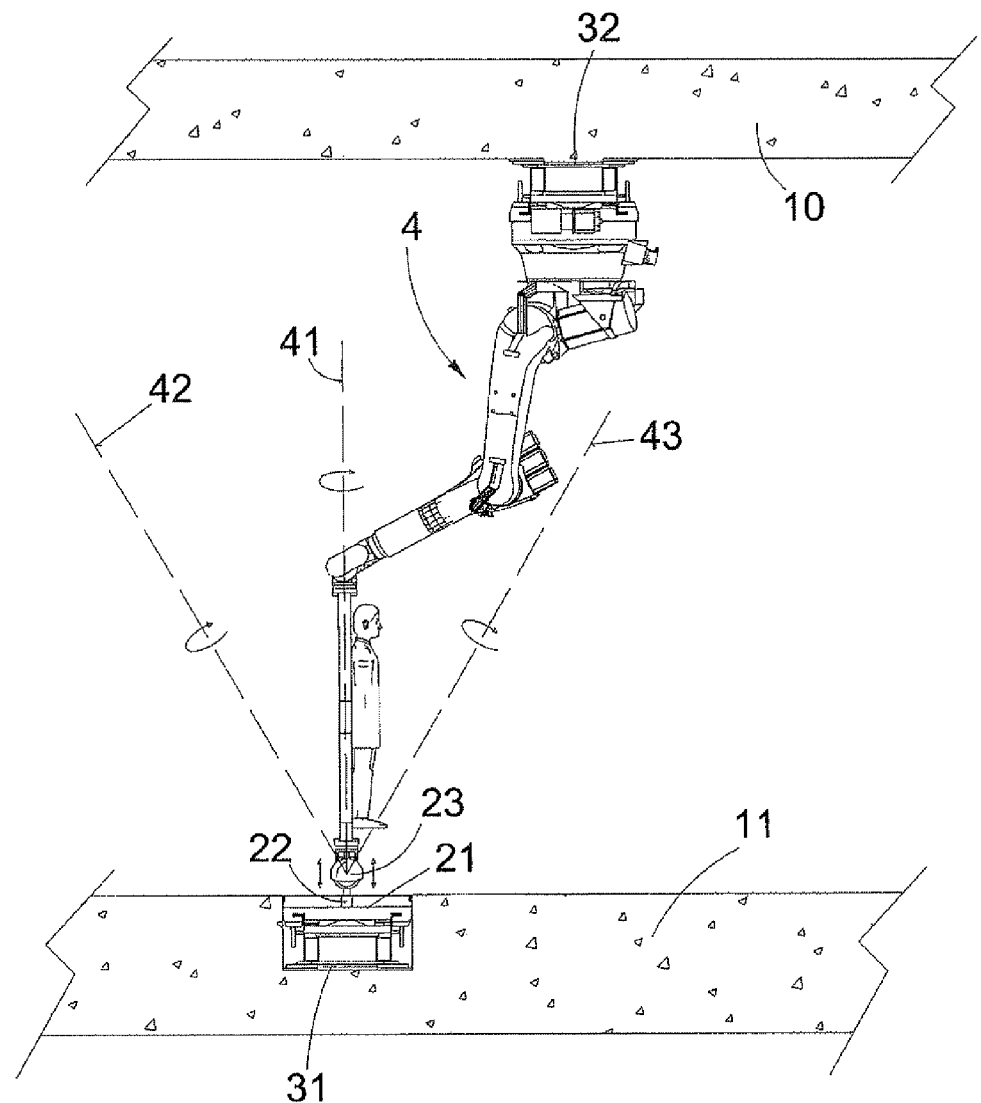

The invention will now be described with reference to a purely exemplifying embodiment (and therefore not limiting) illustrated in the attached figures, where:

FIG. 1 schematically shows a side view of a first embodiment of a robotized system according to the invention, with the treatment couch for the patient in a first position;

FIG. 2 schematically shows a top view of the robotized system of FIG. 1;

FIGS. 3 and 4 show respectively a side view and a top view of the robotized system of FIG. 1, with the treatment couch for the patient in a second position;

FIGS. 5, 6 and 7 schematically show side views of the robotized system of FIG. 1 with the treatment couch for the patient in additional possible positions;

FIGS. 8 and 9 schematically show two side views of a second embodiment of a robotized system according to the invention.

FIG. 1 schematically shows a side view of a first embodiment of a robotized system 1 according to the invention, comprising at least one fixed source of a particle beam, the robotized arms (3, 4), the treatment couch 5 and a logic unit which controls and coordinates the movements of the two robotized arms (3, 4), preferably having six axes of rotation and a horizontal translation axis.

Each end of the treatment couch 5 is connected to the end of one of the robotized arms (3, 4), which are placed on opposite sides with respect to the at least one fixed source so that the at least one particle beam emitted by the at least one fixed source is always included in the space between the ends of the two robotized arms (3, 4).

The at least one fixed source of a particle beam and the logic unit are omitted in the attached figures for simplifying the graphic representation; in addition, the logic unit and the robotized arms (3, 4) will not be described because they are per se known and therefore able to carried out by a technician without recourse to inventive activity.

In the attached figures, the patient is lying on the treatment couch 5 but, departing from the scope of the invention, the patient may be sitting on the treatment couch 5 or on a seat integral with the treatment couch 5.

As can best be seen from the top view of FIG. 2, the robotized arm 3 is movable along a linear guide 31 and the robotized arm 4 is movable along a linear guide 32, parallel to the linear guide 31; without departing from the scope of the invention, the linear guides 31 and 32 may be skew.

In the embodiment described by way of non limiting example in the FIGS. 1 to 7, the linear guide 31 is integral with the floor 11 (FIG. 8) of the room in which the robotized system 1 is installed and the linear guide 32 is integral with the ceiling 10 (FIG. 8) of said room, whereas, without departing from the scope of the invention, the linear guide 31 can be integral with the ceiling 10 of the room in which the robotized system 1 is installed and the linear guide 32 can be integral with the floor 11 of said room or both linear guides (31, 32) can be integral with the ceiling 11 or the floor 10 of the room in which the robotized system 1 is installed. Similarly, the linear guides (31, 32) may be placed between the walls of the room or between a wall and the floor or ceiling.

The robotized system according to the invention allows the positioning of the treatment couch 5 (and the patient fastened to the treatment couch 5) in any position of the space comprised between the two robotized arms (3, 4) without restrictions, limitations and/or "dead areas" due to the robotized arms (3, 4) and/or to the fixed source. The treatment couch 5, and therefore the patient, can be made to axially rotate by 360° around the line joining the ends of the robotized arms (3, 4).

The floor 11 and ceiling 10 are omitted in FIGS. 1 to 7 for simplifying the graphic representation.

The at least one particle beam generated by the at least one fixed source is advantageously parallel to the linear guides 31 and 32 but without departing from the scope of the invention, the at least one particle beam can be perpendicular to the linear guides 31 and 32 or be skew with respect to the guides themselves.

FIGS. 3 and 4 respectively show a side view and a top view of the robotized system of FIG. 1, with the treatment couch 5 in a second position; FIGS. 5, 6 and 7 schematically show side views of the robotized system of FIG. 1 with the treatment couch 5 in additional possible positions.

FIGS. 8 and 9 schematically show two side views of a second embodiment of a robotized system 1 according to the invention, which differs from that shown above in that one of the robotized arms, in the example the robotized arm 3, consists of a carriage 21, moveable along a linear guide 31 parallel to the linear guide 32, along which the other robotized arm 4 slides, and carries a jack 22 which, in turn carries a ball joint 23 to which an end of the treatment couch 5 is connected.

The linear guide 31 is placed in an opening formed in the floor 11 of the room in which the robotized system 1 is installed.

In FIGS. 8 and 9 the linear guide 20 along which the robotized arm 3 moves is parallel to the guide 32, fixed to the ceiling 10 of the room in which the robotized system 1 is installed, along which the robotized arm 4 moves, but without departing from the scope of the invention, the guide 32 can be fixed to the floor 11 of the room in which the robotized system 1 is installed and the guide 31 can be fixed to the ceiling 10 of said room.

The presence of a ball joint 23 allows cost reduction of the robotized system 1 but restricts the movement of the treatment couch 5 that, in the embodiment shown in FIGS. 8 and 9, always remains in a substantially vertical position.

In fact, the treatment couch 5 can rotate by 360° about the axis 41 passing through the end of the other robotized arm (4, 3), it can be vertically translated by the jack 22 and it can swing with respect to the axis 41 about the ball joint 23.

The treatment couch 5 can therefore occupy any position within a cone having the vertex in the ball joint 23 and defined by the half-lines 42 and 43.

The amplitude of the angle at the vertex of the cone depends on the characteristics of the ball joint 23; if the ball joint 23 allows a vertex angle of 180°, the cone becomes a hemisphere.

Without departing from the scope of the invention, the linear guide 31 which carries the carriage 21 may be placed within an opening formed in a side wall of the room in which the robotized system 1 is installed: in this case, the treatment couch 5 is in a substantially horizontal position and can rotate by 360° about the axis passing through the end of the other robotized arm (4, 3), it can be horizontally translated by the jack 22 and it can swing with respect to the axis 41 within a cone, having the vertex in the ball joint 23 and defined by half-lines 42 and 43.

The amplitude of the angle at the vertex of such a cone depends on the characteristics of the ball joint 23: if the ball joint 23 allows a vertex angle of 180°, the cone becomes a hemisphere.

Without departing from the scope of the invention, an expert technician can apply to the robotized system for positioning a patient with respect to a source of a particle beam previously described all the changes and improvements suggested by normal experience and/or the natural development of the art.

The invention claimed is:

1. A robotized system (1) for positioning a patient with respect to at least one source of a particle beam, comprising:
   two robotized arms (3, 4), said robotized arms (3,4) having six axes of rotation and a horizontal translation axis;
   a treatment couch (5) for the patient permanently connected to ends of said robotized arms (3, 4), said treatment couch (5) adapted to axially rotate by 360° around a line joining the ends of the robotized arms (3,4); and
   a logic unit which controls and coordinates movements of the two robotized arms (3, 4), wherein,
   each robotized arm (3, 4) is movable along a respective linear guide (31, 32) fixed to the floor (11), to the ceiling (10) or to a wall of the room wherein the robotized system (1) is installed,
   said at least one source is fixed and outputs a particle beam always comprised within the space between the ends of the two robotized arms (3, 4),
   the treatment couch (5) being apt to be positioned in any position of the space comprised between the two robotized arms (3, 4).

2. A robotized system (1) according to claim 1, characterized in that the two linear guides (31, 32) are parallel or skew each other.

3. A robotized system (1) according to claim 1, characterized in that one of the linear guides (31, 32) is fixed to the floor (11) of the room wherein the robotized system (1) is installed, whereas the other linear guide (32, 31) is fixed to the ceiling (10) of said room.

4. A robotized system (1) according to claim 1, characterized in that both linear guides (31, 32) are fixed to the ceiling (10) or to the floor (11) of the room wherein the robotized system (1) is installed.

5. A robotized system (1) according to claim 1, characterized in that the particle beam generated by the at least one fixed source is parallel or orthogonal to the linear guides (31, 32), or it is skew with respect to said guides.

6. A robotized system (1) according to claim 1, characterized in that one of the robotized arms (3, 4) consists of a carriage (21) movable along a linear guide (31, 32) parallel to the linear guide (32, 31) along which the other robotized arm (4, 3) slides, and carries a jack (22), which in turn carries a ball joint (23) to which an end of the treatment couch (5) is connected.

7. A robotized system (1) according to claim 6, characterized in that the linear guide along which the carriage (21) slides is placed within a hollow formed in the floor (11), in the ceiling (10) or in a side wall of the room wherein the robotized system (1) is installed.

8. A robotized system (1) according to claim 6, wherein said treatment couch (5) can rotate of 360° about the axis (41) passing through the end of the other robotized arm (3, 4), it can be translated by the jack (22) and it can swing with respect to said axis (41) about the ball joint (23) to occupy any position within a cone having the vertex in the ball joint (23), whose vertex angle amplitude depends on the characteristics of the ball joint (23).

9. A robotized system (1) according to claim 8, wherein the ball joint (23) allows a vertex angle of 180°, characterized in that the treatment couch (5) can occupy any position within a hemisphere having the vertex in the ball joint (23).

10. A robotized system (1) according to claim 1, wherein the patient is laying or sitting on the treatment couch (5), or sitting on a seat integral with the treatment couch (5).

11. A robotized system (1) for positioning a patient, comprising:
a particle beam source within a room, the particle beam source generating a particle beam;
a first robotized arm (3) and a second robotized arm (4), each of said first and second robotized arms (3,4) having six axes of rotation and a horizontal translation axis, each of said robotized arms (3,4) having a first distal end and a second distal end;
a patient treatment couch (5) having a first end permanently connected to the first distal end of said first robotized arm (3) and a second end permanently connected to the first distal end of said second robotized arm (4), said treatment couch (5) axially rotatable by 360° around a line joining the first distal ends of the first and second robotized arms (3,4);
a logic unit which controls and coordinates movements of the first and second robotized arms (3, 4);
a first linear guide (31) fixed to one of a floor (11), a ceiling (10), and a wall of the room, the second distal end of the first robotized arm mounted on the first linear guide so that the first robotized arm (3) is movable along the first linear guide (31); and
a second linear guide (32) fixed to one of the floor (11), the ceiling (10), and the wall of the room, the second distal end of the second robotized arm mounted on the second linear guide so that the second robotized arm is movable along the second linear guide (32), wherein,
the particle beam source is fixed and outputs a particle beam always comprised within a space between the distal ends of the first and second robotized arms (3, 4), and
the treatment couch (5) is positionable in any position of the space comprised between the distal ends of the first and second robotized arms (3, 4) such that an entirety of the patient is reachable by the particle beam generated by the particle beam source.

12. A robotized system (1) according to claim 11, wherein the first and second linear guides (31, 32) are parallel to each other.

13. A robotized system (1) according to claim 11, wherein the first linear guide (31) is fixed to the floor (11) of the room and the second linear guide (32) is fixed to the ceiling (10) of the room.

14. A robotized system (1) according to claim 11, wherein both the first and second linear guides (31, 32) are fixed to the ceiling (10).

15. A robotized system (1) according to claim 11, wherein both the first and second linear guides (31, 32) are fixed to the floor (11).

16. A robotized system (1) according to claim 11, wherein the first robotized arm (3) comprises a carriage (21) movable along the first linear guide (31) parallel to the second linear guide (32) along which the second robotized arm (4) slides, and carries a jack (22), which in turn carries a ball joint (23) to which one end of the treatment couch (5) is connected.

17. A robotized system (1) according to claim 16, wherein the linear guide along which the carriage (21) slides is located within a hollow formed in the floor (11), in the ceiling (10) or in the wall of the room wherein the robotized system (1) is installed.

18. A robotized system (1) according to claim 16, wherein said treatment couch (5) can i) rotate of 360° about an axis (41) passing through the end of the second robotized arm (4), ii) be translated by the jack (22), and iii) swing with respect to said axis (41) about the ball joint (23) to occupy any position within a cone having the vertex in the ball joint (23), whose vertex angle amplitude depends on characteristics of the ball joint (23).

19. A robotized system (1) according to claim 18, wherein the ball joint (23) allows a vertex angle of 180°, and the treatment couch (5) can occupy any position within a hemisphere having the vertex in the ball joint (23).

20. A robotized system (1) according to claim 11, further comprising a seat integral with the treatment couch (5).

* * * * *